(12) United States Patent
Eipper et al.

(10) Patent No.: US 8,639,345 B2
(45) Date of Patent: Jan. 28, 2014

(54) DEVICE FOR ELECTROSTIMULATION

(75) Inventors: Carmen Eipper, Gaeufelden (DE); Walter G. Wrobel, Reutlingen (DE)

(73) Assignee: Okuvision GmbH, Reutlingen (DE)

( * ) Notice: Subject to any disclaimer, the term of this patent is extended or adjusted under 35 U.S.C. 154(b) by 0 days.

(21) Appl. No.: 13/549,062

(22) Filed: Jul. 13, 2012

(65) Prior Publication Data

US 2013/0184782 A1   Jul. 18, 2013

Related U.S. Application Data

(63) Continuation of application No. PCT/EP2011/050447, filed on Jan. 14, 2011.

(30) Foreign Application Priority Data

Jan. 15, 2010 (DE) .................... 20 2010 001 150 U
Jul. 8, 2010 (DE) .......................... 10 2010 027 201

(51) Int. Cl.
*A61N 1/04* (2006.01)

(52) U.S. Cl.
USPC ........................................... 607/53; 600/558

(58) Field of Classification Search
USPC ........................................... 607/53; 600/558
See application file for complete search history.

(56) References Cited

U.S. PATENT DOCUMENTS

| 5,154,174 | A | | 10/1992 | Hawlina |
| 5,360,438 | A | * | 11/1994 | Fisher ............................... 607/53 |
| 5,522,864 | A | | 6/1996 | Wallace et al. |
| 6,035,236 | A | | 3/2000 | Jarding et al. |
| 6,275,735 | B1 | | 8/2001 | Jarding et al. |
| 7,020,527 | B2 | | 3/2006 | Morimoto et al. |
| 2004/0176820 | A1 | | 9/2004 | Paul et al. |
| 2004/0230228 | A1 | | 11/2004 | Nakamura |
| 2005/0137649 | A1 | * | 6/2005 | Paul, Jr. .......................... 607/53 |
| 2008/0058793 | A1 | | 3/2008 | Pilla et al. |

FOREIGN PATENT DOCUMENTS

| DE | 36 11 115 | 10/1987 |
| DE | 90 11 254 | 1/1991 |
| EP | 0 325 201 | 7/1989 |
| EP | 1 941 829 | 7/2008 |
| WO | WO-2005/068018 | 7/2005 |
| WO | WO-2005/077452 | 8/2005 |
| WO | WO-2009/142447 | 11/2009 |

OTHER PUBLICATIONS

Gekeler, Florian, et al. "Phosphenes Electrically Evoked with DTL Electrodes: A Study in Patients with Retinitis Pigmentosa, Galucoma, and Homonymous Visual Field Loss and Normal Subjects". Investigative Opthalmology & Visual Science (2006) 47(11), p. 4966-4974.*

Gekeler et al., "Phosphenes Electrically Evoked with DTL Electrodes: A Study in Patients with Retinitis Pigmentosa, Glaucoma, and Homonymous Visual Field Loss and Normal Subjects," Investigative Opthalmology & Visual Science (2006) 47(11):4966-4974.

(Continued)

*Primary Examiner* — Christopher D Koharski
*Assistant Examiner* — Michael Carey
(74) *Attorney, Agent, or Firm* — Morrison & Foerster LLP

(57) ABSTRACT

A device for electrostimulation of the eye is provided with a spectacles-like supporting frame (11) which has a nose part (12) and an arrangement (17, 18), connected to the nose part (12), for holding the supporting frame (11) on the head of the patient, wherein at least one stimulation electrode (26, 27) is arranged on the nose part (12). Furthermore, provision is made for at least two electrode holders (22, 23, 24, 25) on the nose part (12), between which electrode holders an interchangeable, wire-shaped stimulation electrode (26, 27) is clamped (FIG. 1).

28 Claims, 8 Drawing Sheets

(56) References Cited

OTHER PUBLICATIONS

Hawlina et al., "New Noncorneal HK-Loop Electrode for Clinical Electroretinography," Documenta Opthalmologica (1992) 81:253-259.

International Preliminary Report on Patentability and Written Opinion for International Patent Application No. PCT/EP2011/050447, mailed Aug. 7, 2012, 15 pages.

International Search Report for International Patent Application No. PCT/EP2011/050447, mailed Jul. 5, 2011, 18 pages.

* cited by examiner

DEVICE FOR ELECTROSTIMULATION

CROSS-REFERENCE TO RELATED APPLICATIONS

This is a continuation application of co-pending international patent application PCT/EP2011/050447, filed Jan. 14, 2011 and designating the United States, which was published in German as WO 2011/086150 A2, and claims priority to German patent application DE 10 2010 027 201.9, filed Jul. 8, 2010, and German utility model DE 20 2010 001 150.7, filed Jan. 15, 2010. The entire contents of these prior applications are incorporated herein by this reference.

BACKGROUND OF THE INVENTION

1. Field of the Invention

The present invention relates to a device for electrostimulation of the eye, comprising a spectacles-like supporting frame which has a nose part and an arrangement, connected to the nose part, for holding the supporting frame on the head of the patient, wherein at least one stimulation electrode is arranged on the nose part.

2. Related Prior Art

Such a device has been disclosed in US 2004/0176820 A1, now issued as U.S. Pat. No. 7,158,834.

The known device and further devices from the prior art are used to route electric stimulation signals into the eye because it was found that specific forms of macular degeneration and other eye disorders can be stabilized and even improved as a result of this.

Retinal degeneration is a significant cause of blindness in industrialized countries. Various studies provide indications that low electrical currents which flow through the retina can delay the onset of hereditary, age-related or sudden degeneration of the retina.

This opens up the possibility of being able to delay the gradual loss of sight by means of regular, that is to say, e.g., daily or weekly, electric stimulation of the eye in order thus to maintain parts of the vision for longer in affected patients, or even restore parts of the vision.

Expediently, this treatment should be carried out by the patient himself and at home. In doing so, in the extreme case, the assumption must be made that the patient is practically blind. This results in significant demands on the device mentioned at the outset.

The device known from US 2004/0176820 A1, now issued as U.S. Pat. No. 7,158,834, mentioned at the outset, is a type of spectacles with a nose part covering both eyes in the style of a diving mask, with a plurality of electrodes arranged thereon which establish contact with the eye when the spectacles are put on.

To this end, the known spectacles are equipped with a type of elastic band, by means of which the spectacles in the style of a diving mask put on by the patient are held against the head such that they rest tightly against the face around the region of the eye.

A plurality of electrodes are provided around the area of the eye and these establish a punctiform contact to the tissue immediately surrounding the eyes.

It is mentioned that it is also possible to use an individual electrode, which can rest against the closed eyelid or against any other eye tissue.

The electrodes are connected—this is not explained in more detail—to a stimulation instrument which generates electric signals that are routed via the electrodes into the eyes as stimulation signals. The required counter electrode is attached anywhere on the body of the patient.

The inventor of US 2004/0176820 A1, now issued as U.S. Pat. No. 7,158,834, reports that various forms of retinal degeneration can be halted, with the state of the patient sometimes even improving again, through use of the known spectacles when stimulation signals of specific frequencies, currents and voltage ranges are applied.

A similar approach is adopted by the device described in PCT Patent Publication No. WO 2005/077452 A1, which likewise makes possible the electrostimulation of the eye.

In this device, the electrodes are embodied in the form of foam pads which are placed onto the closed eyelids. The counter electrode is connected to the hand of the patient.

A stimulation instrument is also connected to the electrodes in this case in order to route electric stimulation signals into the eyes.

U.S. Pat. No. 5,522,864 A also describes the use of a foam electrode, to be placed onto the closed eyelid, for electrostimulation on the eye, with the electrode and, optionally, parts of the stimulation electronics being attached to the head of the patient by a headband.

U.S. Pat. No. 6,035,236 A and U.S. Pat. No. 6,275,735 B1 describe methods for electrostimulation, in which stimulation signals are applied to specific stimulation points on the skin around the eye.

European Patent Application No. EP 0 325 201 A2, now abandoned, describes a stimulation instrument for improving vision, which comprises a spectacles-like supporting frame, on which a sprung element is arranged, which presses a plate against the closed eyelid. Provided on the plate there is an areal electrode, which lies on the closed eyelid and emits stimulation signals.

The issued patent DE 90 11 254 U describes therapeutic spectacles for electrical stimulation of specific areas of skin around the eye. Electrode plates have been introduced into the spectacles and these come into direct contact with the areas of skin to be stimulated when the spectacles are put on.

A disadvantage of all devices described insofar is that the electric stimulation of the eye is brought about by electrodes placed onto the skin, as also already known from other fields of application of electrostimulation.

Thus, electrostimulation in general was already proposed as early as the $18^{th}$ century for the treatment of very different clinical pictures, including eye disorders as well. Very different embodiments for the utilized electrodes were proposed in the process.

One embodiment option consists of looking with opened eyes into a water bath consisting of physiological saline, wherein the water bath contains electrodes that are connected to the stimulation instrument. This method is called iontophoresis. However, due to the difficulties associated therewith, iontophoresis has not found widespread use.

Electrodes applied to the eyes are also used in electroretinography (ERG). In this ophthalmological diagnosis method, electrodes are attached in the vicinity of the eye, flashes of light are guided into the eye and the corresponding nerve currents through the optical nerve are measured at the electrodes.

Within the scope of applying ERG, it was found that there are large variations in the signal amplitude if use is made of electrodes applied to the skin and that the signal amplitude depends on the current state of the skin, i.e., on the fat content thereof, on the moisture thereof and, for example, the fact whether it was recently washed.

These effects are not very bothersome for ERG because the electrodes in this case are used to conduct away measurement currents where the time profile of the signals is of interest.

However, these effects are unacceptable for the therapeutic application planned within the scope of the present application. This is because if the skin resistance is very different from application to application, it proves impossible to ensure that the electric field strength generated on the retina is reproducible and that therapeutic success can be expected.

Furthermore, in order to avoid these effects, electrodes are preferably also used in ERG which establishes direct contact with moist body surfaces, which is of low resistance. Therefore, in ophthalmology, the stimulation electrode generally contacts the cornea, i.e., the eye surface. A large area counter electrode is then applied to the skin, the large area of which ensures a low contact resistance and hence reproducible conditions.

Eye electrodes known from ERG first of all include metallically coated contact lenses, as are used in U.S. Pat. No. 7,020,527 for electrostimulation. These contact lenses are considered to be difficult to tolerate and painful because the curvature thereof is not precisely fitted to the eye for reasons of costs.

U.S. Pat. No. 5,154,174 A has disclosed the use of bent wire loops as electrodes for ERG, which are inserted into the conjunctival sac of the eye. These electrodes, which are also known as Hawlina electrodes, are significantly more tolerable than the metallically coated contact lenses, but are difficult to handle for blind patients because they cannot monitor the precise shape and the seat of the wire loop. Adhesive plasters are generally used for fixation to the head, which is disadvantageous in that the position of the electrode can change over the whole duration of the stimulation.

So-called DTL electrodes, as offered by Diagnosys LLC, Lowell, Mass., USA, have also found widespread use in ERG.

These DTL electrodes consist of a fine wire, which is placed onto the cornea such that it lies on the eyelid/cornea edge and has good contact to the cornea. The wire is attached with plasters to the left and right of the treated eye.

These electrodes have been tested many times in ERG, they are the most tolerable of all the known ERG electrodes, but are disadvantageous in that the medical practitioner or orderly requires great manual dexterity for the application thereof in clinical practice. A patient generally does not have this ability, particularly if the patient is blind. Hence these electrodes cannot be applied independently by patients.

SUMMARY OF THE INVENTION

In view of the above, it is one object of the present invention to improve the device mentioned at the outset such that it establishes a good, reproducible contact between the stimulation electrode and the eye to be treated but, at the same time, can also be used at home without problems by a blind or almost blind patient.

In the device mentioned at the outset, this and other objects are achieved in that at least two electrode holders are provided on the nose part, between which electrode holders an interchangeable, wire-shaped stimulation electrode is clamped.

The inventor of the present application has identified that it is possible to combine the type of positioning and the good tolerability and the good and reproducible electric contact of a wire-shaped electrode, more particularly a DTL electrode, with a device for stable and precise positioning on the head or eye of the patient.

This device is, at one occasion, accurately fitted to the respective patient by a person skilled in the art, which patient then only has to hang a premade wire electrode into the electrode holders and put on the device and connect it to a stimulation instrument.

Thereafter the device should be connected to the stimulation instrument in a known fashion, whereupon the treatment can commence.

The type of the utilized stimulation instrument and the signal shape of the utilized stimulation signals are not the subject matter of the present invention; they need only be suitable for the electrostimulation of the retina. Hence, use can for example be made of stimulation instruments and signal shapes which are described in the documents US 2004/0176820 A1, now issued as U.S. Pat. No. 7,158,834, PCT Patent Publication No. WO 2005/077452 A1, issued U.S. Pat. No. 5,522,864 A, U.S. Pat. No. 6,035,236 A and U.S. Pat. No. 6,275,735 B1, mentioned at the outset.

Any wire electrodes, but preferably DTL electrodes as can be purchased for example from Diagnosys LLC (mentioned at the outset), can be used as stimulation electrode in this case. The stimulation electrode is preferably made of a precious metal, a stainless steel alloy or a metallically coated polymer thread. By way of example, a fine, silver-coated nylon or polyamide thread has proven its worth.

The stimulation electrodes are interchangeable, and so dirtied or defective stimulation electrodes can be replaced by new ones without needing to acquire and fit a new device. This is particularly advantageous from the point of view of costs.

According to one object, the stimulation electrode is connected to at least one of the electrode holders in an electrically conductive fashion, wherein, more preferably, at its free end, each electrode holder is provided with a receptacle for the stimulation electrode.

Here, it is advantageous that the sensitive stimulation electrode is only attached and simultaneously contacted when it is being interchanged, thereafter the electrical connection to the stimulation instrument is brought about via the electrode holders, onto which, for example, a connection cable is always clamped if the device is used.

However, it is preferable if a cable is connected to at least one of the electrode holders, wherein the cable preferably is either embodied as connection cable for the direct connection to a stimulation instrument or connected to a connection tab arranged on the device.

This measure increases the operating comfort and the operational safety. After putting on the device, the patient only still needs to connect the connection cables already present on the electrode holders to the stimulation instrument.

If connection tabs for connecting the connection cables are provided on the device, it is easier to store the device after use, with the electrode holders also being better protected because the connection cables can be removed before this. Furthermore, there is a type of tensile relief during use because the connection cables do not "pull" directly on the electrode holders.

According to another object, the electrode holders are embodied with an elastically resilient, elongate body, which is preferably embodied as a helical spring and/or made of a flexible polymer, wherein each electrode holder preferably has a mount, by means of which it is arranged on the nose part in an adjustable and interchangeable fashion.

In this case, it is advantageous that, when the device is put on and when, in connection therewith, the stimulation electrode is placed onto the cornea, the electrode holders bend under the tension of the bending stimulation electrode such that, on the one hand, they hold the stimulation electrode tightly stretched but, on the other hand, do not exert too much pressure on the cornea.

Furthermore, different patients may require different electrode holders, both in terms of length and flexibility and adjustability. Thus, different electrode holders, which are interchangeable, are stored for the supporting frames, which are only required in limited numbers.

In view of the above, a further object of the present invention concerns an electrode holder for the novel device, which electrode holder has an elastically resilient, elongate body, which, at its one end, has a mount for assembling the electrode holder on a frame of the device and, at its other end, has a receptacle for a wire-shaped stimulation electrode.

As per a further object, the electrode holders are embodied as pins, preferably made of V2A stainless steel, wherein, preferably, the at least one stimulation electrode is fixedly connected to one of the pins and, at the other pin, it is guided through an ear and subjected to tension, preferably by a weight.

In this case, it is advantageous that use is made of electrode holders that are easily assembled and easy to set but are so stable that they are not bent or adjusted when the stimulation electrodes are interchanged.

Furthermore, the use of weights simplifies the placing of newly utilized stimulation electrodes onto the eye such that this can even be undertaken independently by a very visually impaired patient.

According to still a further object, the at least one stimulation electrode is embodied as a loop, which is connected to a weight and, prior to use of the device according to the invention, is merely hooked into the two electrode holders such that the stimulation electrode extends between the two electrode holders and is tensioned by the weight hanging below and between the electrode holders.

To this end, the electrode holders are embodied as pins made of an electrically conductive material, which respectively have an upwardly open groove at their inner free end facing the patient, into which groove the stimulation electrode can also be hooked by a very visually impaired or even blind patient.

In order to further simplify the hooking-in or placing of the stimulation electrode, the pin can respectively be provided with at least one area running obliquely toward the groove, on which area the stimulation electrode placed thereon slips into the groove.

The electrode holder which is adjustable in its longitudinal direction can in this case be attached to the device in a height-adjustable fashion, for which purpose provision is preferably made for a further pin, which, at its one end, is arranged on the device in a height-adjustable fashion and, at its other end, carries a further pin, which can be adjusted perpendicularly to the further pin and, at its free end facing the patient, is embodied to hold the stimulation electrode.

The supporting frame and the electrode holders can then, at one occasion, be fitted to the shape of the head and the face of the patient by a normal-sighted person. Thereafter, even practically blind patients can hook the stimulation electrodes into the electrode holders and put on the supporting frame in a precise and reproducible fashion. In the process, the stimulation electrodes rest against the eye to be treated such that they come to rest on the cornea and between the edges of the lids.

Thus, the stimulation electrodes are interchangeable and disposable.

In view of the above, another object of the present invention concerns a stimulation electrode for use with the novel device, which stimulation electrode is embodied as a loop made of a metallically coated polymer thread and connected to a weight.

Finally, it is preferable if the nose part has a nose bracket and at least one frame or eye bracket, on which the two electrode holders are arranged, wherein, preferably, the arrangement for holding the supporting frame has two lateral arms attached to the nose part, which lateral arms are hinged on the nose part in a flexible and/or foldable fashion.

Here, the nose bracket can be arranged in adjustable fashion with respect to the frames or eye brackets, preferably be adjustable on a nose holder via a holding pin, on which nose holder two eye brackets are secured, at least one of which is provided with two pin holders which sit in displaceable fashion on the eye bracket and each of which carry a height-adjustable holding pin on which respectively one electrode holder, which can be adjusted in its longitudinal direction, is held.

A receptacle for the stimulation electrode, preferably an upwardly open groove, is provided at the free end, facing the patient, of every electrode holder. Here, the selected design renders it possible for the free end with the receptacle to be adjustable with respect to the eye bracket in the three spatial directions.

It is advantageous in this case that the supporting frame in the style of spectacles can be fitted well to the shape of the head of the patient, and that, nevertheless, a good adjustment and alignment of the electrode holders with respect to the eyes of the patient is possible.

As an alternative to the embodiment of the supporting frame as spectacles with a nose bracket, frame or eye bracket and lateral arms, the spectacles-like supporting frame can also be embodied as facemask.

Within the scope of the present innovation, a facemask is understood to mean a mask-like structure, which rests flat against the face of the patient at least in the region of the forehead, the cheeks and the nose, wherein a fitted eye opening is provided for the eye. The facemask can cover both sides of the face, wherein it can also cover the forehead and temples and upper-jaw region. In this case, corresponding openings are also provided for the ears.

Such facemasks are, on one occasion, fitted to the geometry of the head of the patient by a person skilled in the art, for example in a medical-supply store or an orthopedics store, such that the patient can then put them on in a reproducible fashion.

These days, facemasks are used in order to stabilize the nose after, e.g., a nasal fracture and protect it against mechanical influences. By way of example, they are used by football players.

The use according to the invention of a facemask now renders it possible for the patients to always put on this facemask in a reproducible fashion such that the stimulation electrode attached thereto also rests against the cornea in a reproducible fashion and runs along the lower eyelid.

The facemask itself consists of a thermoplastic which can be well fitted to the shape of the face of the respective patient.

As known per se, the facemask is affixed to the head of the patient with adjustable rubber bands, elastic bands or VEL-CRO™ hook-and-loop fasteners.

A particular advantage of using the face mask is that the position of the facemask and hence the position of the utilized stimulation electrode remains unchanged over the whole duration of the stimulation because the facemask is held in immobile fashion by fitting it to the contour of the head of the patient and by attaching it to the head.

Then, the patient only still needs optionally to clamp new stimulation electrodes into the electrode holders and ensure that the electrodes run along the lower eyelid.

In the process, it is preferable for at least one electrode holder to be embodied as a snap fastener with lower part and upper part, wherein the lower part is secured on the facemask.

The use of snap fasteners is advantageous, particularly from a handling point of view, because they allow a simple attachment of stimulation electrode and connection cables on the facemask. This attachment can be brought about on one occasion by a person skilled in the art such that the snap fasteners need not be opened during use. However, visually impaired or even blind patients are also able to close and reopen a snap fastener, and so they can, if need be, even themselves assemble or replace stimulation electrodes and/or connection cables on the facemask.

Furthermore, it is preferable if either the upper part or the lower part of the snap fastener is fixedly connected to a connection cable.

Here it is advantageous that provision is made for a good tension relief for the connection cable by means of which the connection to the stimulation instrument is brought about.

The closed snap fastener offers a secure seat for the connection cable such that even movements of the head and hence tensile forces exerted on the facemask by the connection cable do not lead to the facemask slipping. In other words, the position of the stimulation electrode remains unchanged even if the head moves.

The connection cable can conceivably be connected in a simple fashion to the upper part or lower part of the snap fastener by virtue of the fact that the connection cable is either soldered onto the lower part or upper part or else provided with a connection ear which is clamped between the upper part and the lower part of the snap fastener.

Here, use can be made of the conventional design of a snap fastener, the lower part and upper part of which are usually connected by teeth via an attachment part to the fabric which should be connected to another fabric to which part of the snap fastener is likewise secured by teeth via an attachment part. This has been known for a long time and is described in, e.g., DE 36 11 115 A1.

Instead of a fabric, a connection cable can now also be connected to the upper part or lower part of the snap fastener, for example via an ear.

Thus, while the connection cable is either clamped in a fixed but detachable fashion between upper part and lower part of the snap fastener or permanently connected thereto, the stimulation electrode can first of all likewise be clamped between upper part and lower part such that it can be replaced if need be. This replacement can either be undertaken by the patient himself, or else it can be brought about by a person skilled in the art. As long as there is no need to replace the stimulation electrode, the patient can put on and take off the facemask any number of times, with the correct position of the stimulation electrode remaining ensured.

However, the stimulation electrode can also be connected to the attachment part of the lower part, for example via a clamping end, which is secured on the facemask in a permanent or replaceable fashion.

The use of a snap fastener as attachment means thus, on the one hand, enables the fast and problem-free replacement of the stimulation electrode, but, on the other hand, also ensures that the positioned stimulation electrode does not shift its position with respect to the facemask when the facemask is put on and taken off again.

In general, it is preferred in this case if at least one eye opening for an eye of a patient is provided in the facemask and respectively one snap fastener is arranged on both sides next to the eye opening and the stimulation electrode runs through the eye opening between the two snap fasteners and is held by the snap fasteners.

In this case, it is advantageous that the stimulation electrode can be positioned and held in position in a particularly simple fashion. Within the scope of the present invention, "on both sides next to the opening" is understood to mean that one snap fastener is arranged toward the nose side of the eye opening and the other snap fastener is arranged toward the temple side of the eye opening.

If in the devices described insofar use is made of two stimulation electrodes, the circuit can be closed over these two stimulation electrodes, which, it follows, are connected in series and are both connected to the stimulation instrument via their own connection cable.

If use is made of only one stimulation electrode, or if the two stimulation electrodes are electrically connected in parallel, provision is made for a counter electrode, which preferably rests against the region of the temple of the patient and is connected to the stimulation instrument via a connection cable secured on the device.

Further advantages emerge from the description and the attached drawing.

It is understood that the features mentioned above and yet to be explained below can be used not only in the respectively specified combination, but also in other combinations or on their own, without departing from the scope of the present invention.

BRIEF DESCRIPTION OF THE DRAWINGS

Embodiments of the invention are illustrated in the drawing and will be explained in more detail in the following description, in which.

DESCRIPTION OF PREFERRED EMBODIMENTS

Figure 1:
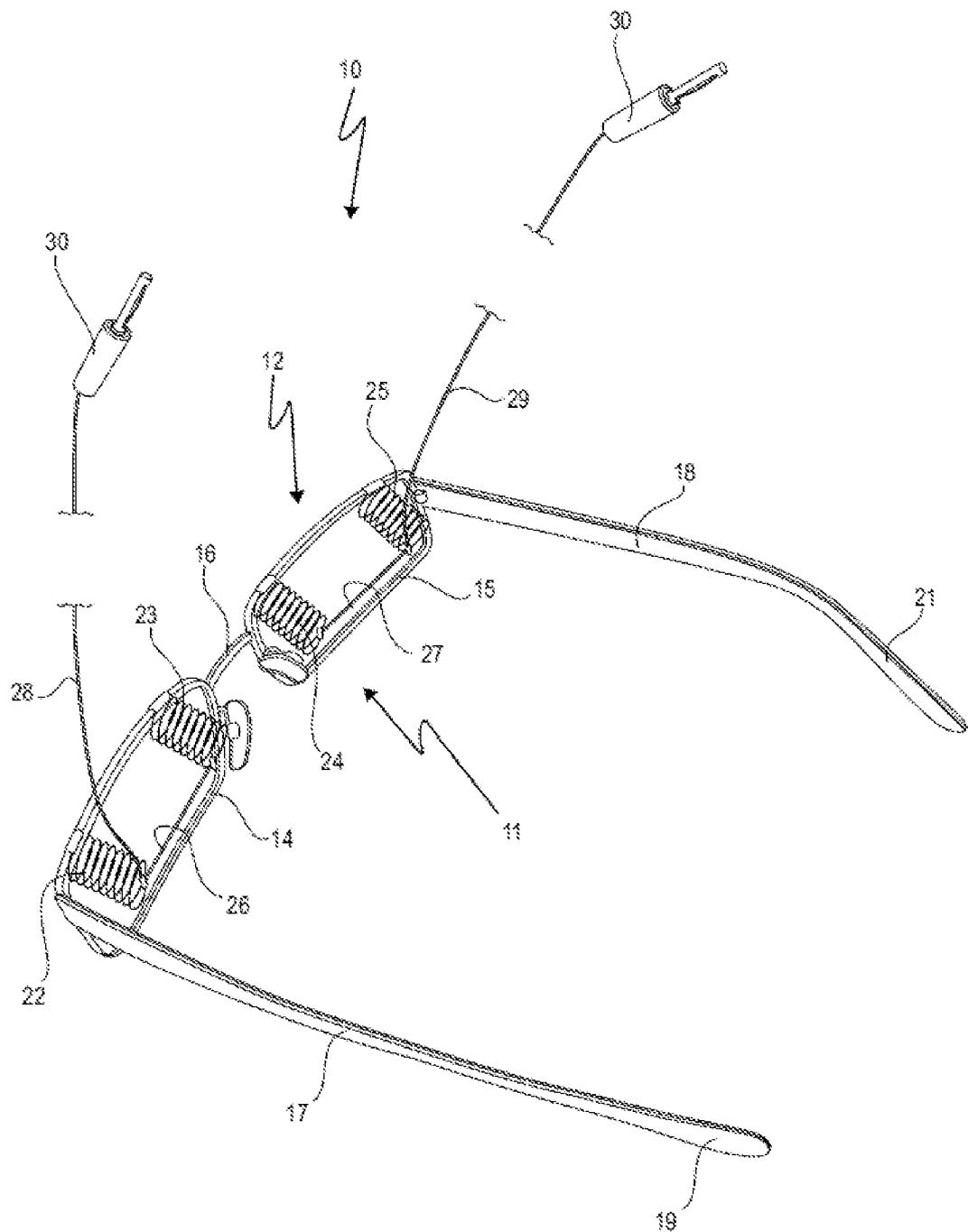
FIG. 1 shows a schematic perspective illustration of the novel device, by means of which both eyes are treated.

In FIG. 1, a device denoted by 10 is shown, which serves for electrostimulation of the eye. The device 10 comprises a spectacles-like supporting frame 11, which has a nose part 12, on which two frames 14 and 15 are formed which correspond to the position of the eye of the patient. The two frames 14 and 15 are interconnected by a nose bracket 16.

As conventional with spectacles, the nose part 12 is provided with an arrangement for keeping the supporting frame 11 on the head of a patient. This arrangement has two lateral arms 17 and 18, which are hinged on the nose part 12 in a foldable fashion and have a bent embodiment at their respective free end 19 and 21 such that the supporting frame 11 can be fitted to the physiognomy of a patient in an optimum fashion.

Two elastically resilient electrode holders 22 and 23, and also 24 and 25, are provided on each frame 14 and 15, said electrode holders being sprung in the direction of the lateral arms 17 and 18 and also perpendicular thereto.

The electrode holders 22, 23, 24, 25 are embodied such that respectively one wire-shaped stimulation electrode 26 and 27, respectively, can be clamped therebetween, said stimulation electrode being connected to the respectively outer electrode holder 22 and 25, respectively, in an electrically conductive fashion. The electrode holder 22 and the electrode holder 25 are respectively connected to a connection cable 28 or 29, which respectively has one plug 30 at the free end thereof, by means of which the electrode holders 22 and 25 and hence the wire-shaped stimulation electrodes 26 and 27 can be connected to both poles of a stimulation instrument, as will be described further below in conjunction with FIG. 2.

The electrode holders 22, 23, 24, 25 are embodied such that they are sprung in the longitudinal direction, but can also be displaced laterally. In the simplest case, the electrode holders are pure helical springs, which are attached to the frames 14 and 15 in a suitable fashion.

When the spectacles-like supporting frame 11 has been fitted in suitable fashion to the physiognomy of the patient, the electrode holders 22, 23, 24, 25 lie level with the eye, and to the left and right thereof and protrude such that they almost contact the lid corners when the device 10 is put on.

In order to avoid the risk of injury, the protruding ends of the electrode holders 22, 23, 24, 25 have a rounded-off design where they carry the stimulation electrode 26 or 27.

The electrode holders 22, 23, 24, 25 can be adjusted to the eye position, for the purpose of which they are attached to the frames 14 and 15 by means of displaceable coupling sleeves and fixing screws (not illustrated in the figure). In the process, it is possible for there to be not only an adjustment in the spacing between the electrode holders 22, 23 or 24, 25, i.e., an adjustment toward and away from one another, but also an adjustment perpendicular to their spacing and tilting in every direction about their longitudinal axis. The spacing and the longitudinal axes are illustrated at 31 and 32 in the plan view of FIG. 2, and the tilting movement in a plane is illustrated by arrows 33.

In order to enable optimal fitting to the individual patients, the electrode holders 22, 23, 24, 25 are arranged on the frames 14, 15 in an interchangeable fashion such that, depending on need, use can be made of longer or shorter electrode holders 22, 23, 24, 25.

Figure 2:
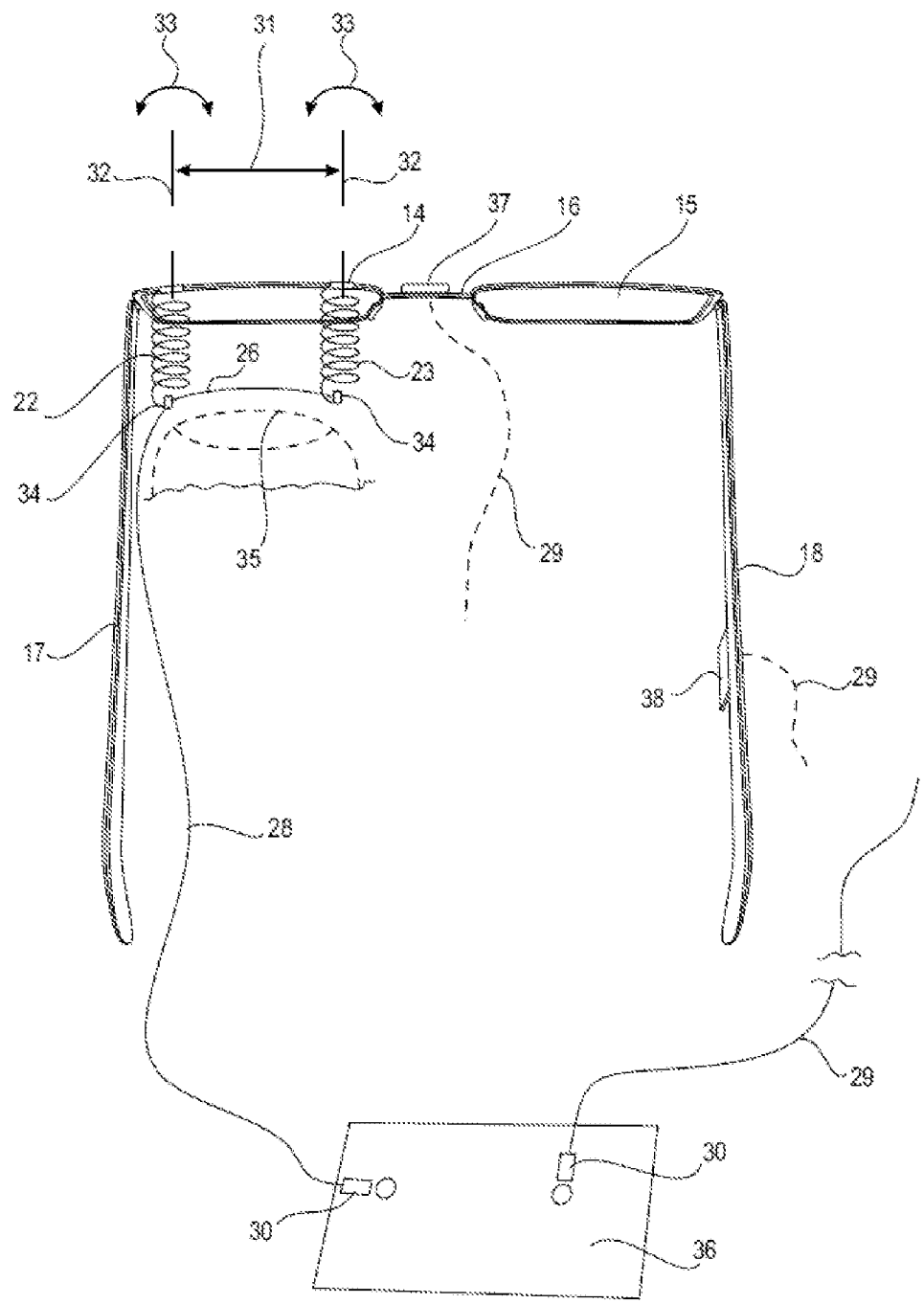
FIG. 2 shows a plan view on the device from FIG. 1.

At their free end situated toward the eye, the electrode holders 22, 23, 24, 25 contain suitable receptacles, into which the patient can insert the stimulation electrodes 26 and 27. By way of example, the wire-shaped stimulation electrodes 26, 27 can be secured by a click-fastener or any other suitable latching. In FIG. 2, these receptacles for the two electrode holders 22 and 23 are indicated at 34.

The electrode holders 22 and 23 or 24 and 25 can be tilted slightly to the outside such that they tighten the stimulation electrode 26 or 27 therebetween. This tension in the stimulation electrode 26, 27 can also be achieved by the connection cable 28, 29, which leads from the stimulation electrode 26, 27 to the stimulation instrument.

The plan view of FIG. 2 shows the situation when the device 10 was put on by the patient such that the wire-shaped stimulation electrode 26 rests against the cornea, indicated at 35, of the eye. In doing so, the stimulation electrode 26 curves such that it rests in fitting fashion against the curvature of the cornea 35. This is possible because the electrode holders 22, 23 have such a flexible design that they can easily be pulled inward when the stimulation electrode 26, 27 is placed against the cornea 35.

It should also be noted that in FIG. 2, for reasons of clarity, the stimulation electrode 26 with the electrode holders 22 and 23 is only shown for the frame 14. The frame 15 can have an equivalent design, wherein it is also possible to only provide one of the two frames 14, 15 with a stimulation electrode 26 or 27, for example if only one eye of the patient should or needs to be treated.

When the device is correctly positioned on the nose and ears of the patient, the stimulation electrode 26, 27 initially touches the cornea 35 at its front-most point when said device is put on. When the device is put on further, the stimulation electrode 26, 27 then rests against the cornea 35 because the electrode holders 22, 23, 24, 25 have a sufficiently resilient design.

Figure 3:
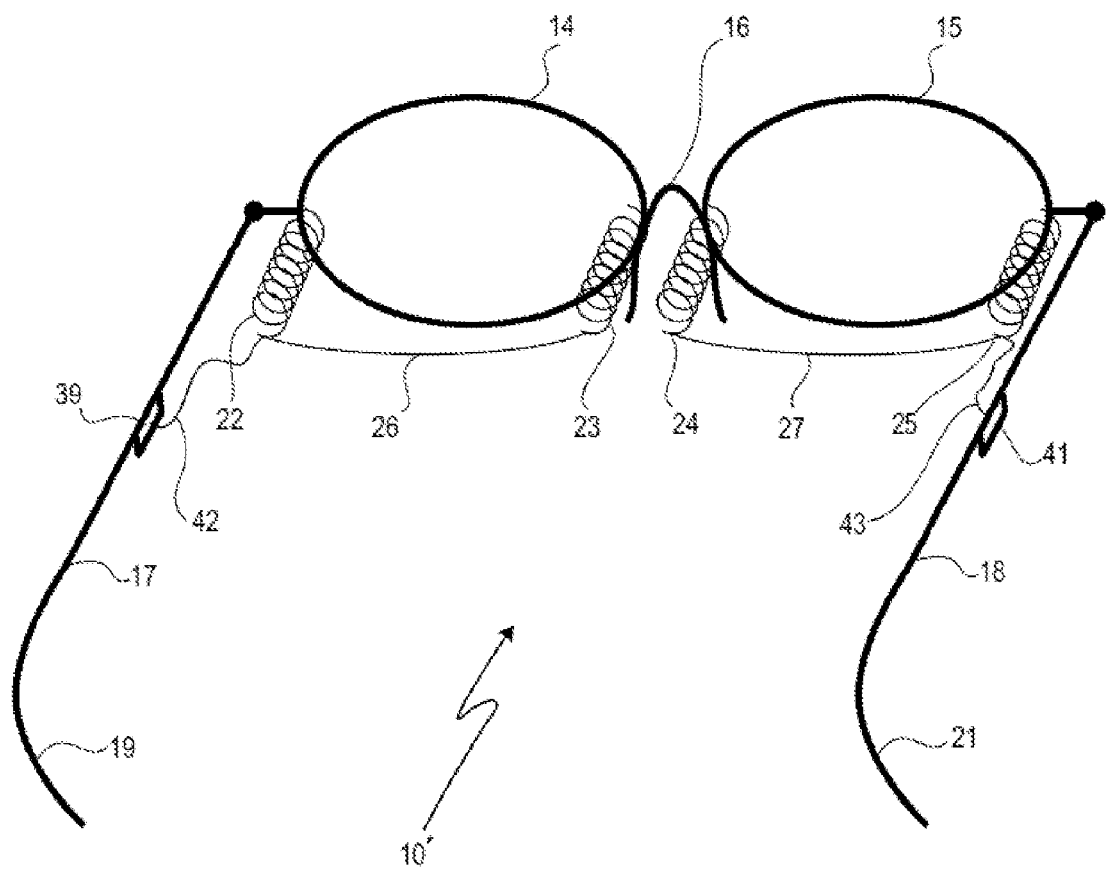
FIG. 3 shows an alternative embodiment of the device from FIG. 1.

Instead of the helical springs shown in FIGS. 1 to 3, the electrode holders 22, 23, 24, 25 can also be produced from elastically resilient polymer material.

The stimulation electrodes themselves can consist of various materials. Precious metals (Pt, Pd, Ir, Ag, Au, etc.) and also stainless steel alloys are feasible. Polymer threads coated by precious metals are also suitable; by way of example, these are used in DTL electrodes. In respect of further embodiments of the electrodes, reference is made in an exemplary fashion to Hawlina and Konek: "New noncorneal HK-loop electrode for clinical electroretinography", *Documenta Ophthalmologica* 81: 253-259, 1992, and the references contained therein.

After the supporting frame 11 is put on and the stimulation electrode 26, 27 is fitted to the cornea 35, the connection cables 28, 29 are connected to a stimulation instrument 36.

Thereafter the patient closes the eye to be treated for the duration of the subsequent treatment such that the stimulation electrodes 26, 27 lie on the cornea 35 and between the lid edges. In this fashion the stimulation electrodes 26, 27 are surrounded on all sides by moist, i.e., electrically well-contacted, tissue.

In respect of the precise embodiments of the stimulation instrument 36 and the signal shapes of the stimulation signals, reference can be made to the documents discussed at the outset, wherein the prior art has also disclosed other stimulation instruments and signal shapes for stimulation signals by means of which, e.g., the retina of a patient can be stimulated.

In the device 10 from FIG. 1, each eye is contacted by a stimulation electrode 26, 27, wherein the respectively other electrode 27, 26 acts as a counter electrode, the circuit is, as it were, closed over both eyes of the patient. In other words, there is no need for an additional ground or counter electrode, which makes the use very simple for the patient.

The use of the respectively other stimulation electrode 27, 26 as counter electrode is also possible because use is made during the electric stimulation either of alternating currents or of so-called biphasic pulses.

However, if the device 10 is designed to stimulate only one eye, a counter electrode 38 is arranged either on the nose bracket 16 or on one of the lateral arms 17, 18, from which counter electrode the second connection cable 29 emanates, as shown in FIG. 2.

FIG. 3 shows a further embodiment of the novel device 10', in which the frames 14 and 15 are fitted in oval fashion to the shape of the eye, which enables a particularly simple adjustment of the electrode holders 22, 23, 24, 25.

In FIG. 3, use has been made of the same reference signs as in FIG. 1, and so reference is made to the description above in respect of the further details.

In the device 10', connection tabs 39, 41 are provided on the lateral arms 17, 18, with the stimulation electrodes 26, 27 being connected to said connection tabs via cables 42, 43. The connection cables 28, 29 are then connected, e.g., clamped or inserted, to the connection tabs 39, 41.

In contrast to the device 10 of FIG. 1, the lateral arms 17, 18 are not hinged to the frames 14, 15 in a foldable fashion in the device 10', but rather these arms are intrinsically flexible such that the supporting frame 11 can be put on in a comfortable fashion and is held on the head. The adaptation to the head of the patient in this case is also brought about via the bent ends 19, 21, which, optionally after heating, can be bent and curved such that the supporting frame 11 is fitted to the physiognomy of a patient in an optimal fashion.

As mentioned previously, the electrode holders 22, 23, 24, 25 can be interchanged in order firstly to be able to replace defective electrode holders 22, 23, 24, 25 and secondly also to be able to assemble the electrode holders 22, 23, 24, 25 fitting the shape of the face of the patient onto one and the same supporting frame 11.

Figure 4:
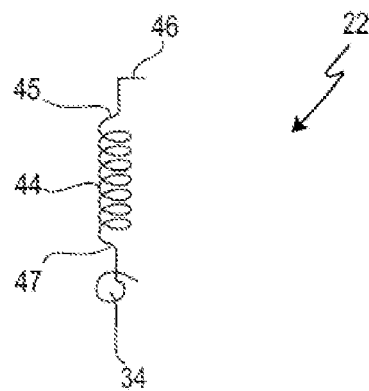
FIG. 4 shows an electrode holder, which is used in the devices from FIGS. 1 to 3.

Such an electrode holder 22 is shown in FIG. 4 in an exemplary fashion. It has an elongate, elastically resilient body 44 which, on its one end 45, carries a mount 46, by means of which it can be attached to the frame 14 or 15. In this case, a screw-in connection is possible.

At its other end 47, the electrode holder 22 carries the aforementioned receptacle 34, on which the stimulation electrode 26, 27 is attached.

The body 44 is embodied as a helical spring which is made of a resilient polymer. The body 44 can also be embodied as a spring tab.

As an alternative to the embodiment of the supporting frame 11 as spectacles with frames 14, 15, nose bracket 16 and lateral arms 17, 18, the spectacles-like supporting frame 11 can also be embodied as a facemask.

Within the scope of the present innovation, a facemask is understood to mean a mask-like structure in the style of a mask as used these days in order, e.g., after nasal fractures, to stabilize the nose and protect the latter against mechanical influences.

Figure 5:
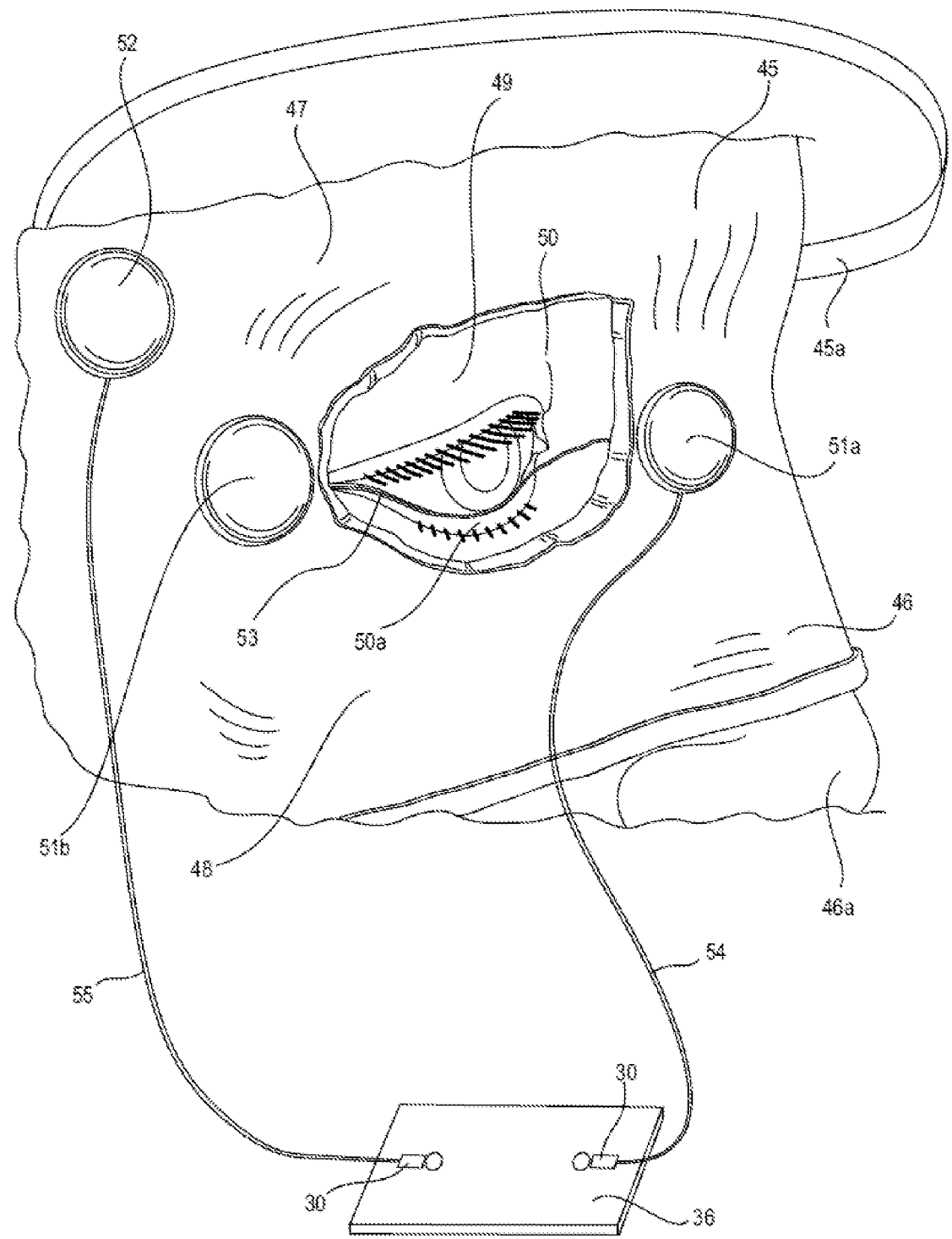
FIG. 5 shows a sketch-like perspective and sectional illustration of a facemask, on which a stimulation electrode is arranged and held by snap fasteners.

FIG. 5 shows such a facemask 45 in a schematic and sectional fashion, said facemask having a nose part 46 which has an integral design with the facemask 45. The facemask 45 is held on the head of the patient by means of an elastic band 45a.

The facemask 45 rests flat against the nose 46a of the patient with the nose part 46, with a forehead part 47 and a cheek part 48 resting flat against the forehead or cheek and temple of the patient.

At least one eye opening 49 is provided in the nose part 46, which opening leaves the eye 50 of the patient uncovered when the facemask 45 is put on. The facemask 45 can, of course, also have two eye openings 49.

The facemask 45 consists of a thermoplastic polymer and is, for example, accurately fitted to the shape of the head of the patient in a medical-supply store, as is done, for example, for athletes in order to protect the nose after a nasal fracture.

Next to the eye opening 49, a first snap fastener 51a is attached to the facemask 45 on the nose side, while a second snap fastener 51b is provided on the other side of the eye opening 49, i.e., on the temple side. A third snap fastener 52 is arranged in the temple region of the facemask 45, i.e., on the cheek part 47.

Extending between the snap fasteners 51a and 51b there is a stimulation electrode 53, which, within the facemask 45, i.e., below the eye opening 49 as it were, runs through said facemask along the bottom by the eyelid 50a of the patient such that the snap fasteners 51, 52 act as electrode holders.

The snap fastener 51 is connected to a connection cable 54, which leads to the stimulation instrument 36, which was already described in conjunction with FIG. 2, to which it is connected by a plug 30, as also already explained in conjunction with FIGS. 1 and 2.

Figure 7:
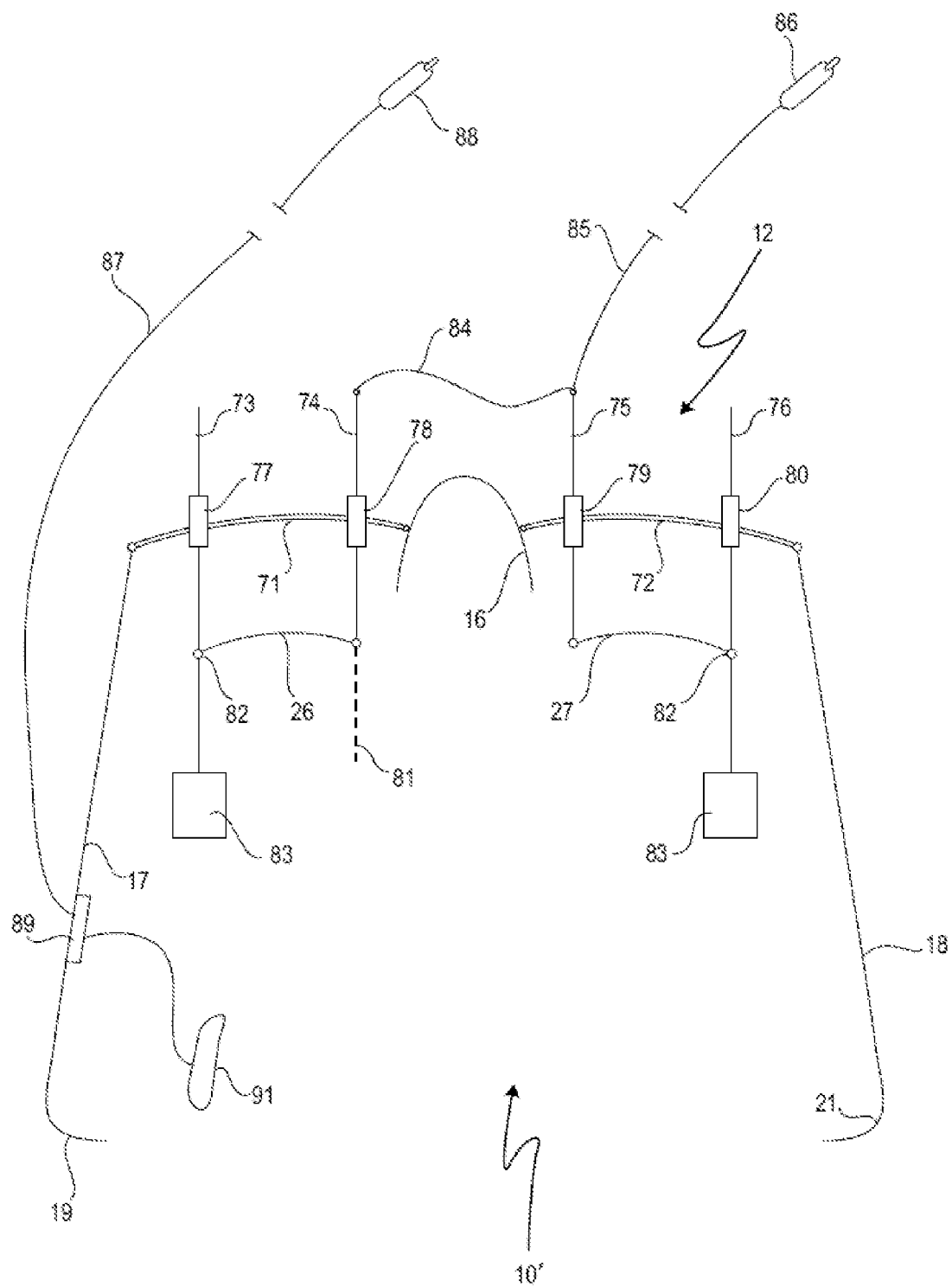
FIG. 7 shows a further alternative embodiment of the device from FIG. 1.

The snap fastener 52 is provided for the counter electrode, the former is, within the facemask 45, connected to a contact area which rests against the temple of the patient when the facemask is put on. The counter electrode is shown in FIG. 7 in conjunction with a further exemplary embodiment of the novel device 10'. Via a connection cable 52 with a plug 30, the snap fastener 52 is connected to the stimulation instrument 36.

Figure 6:
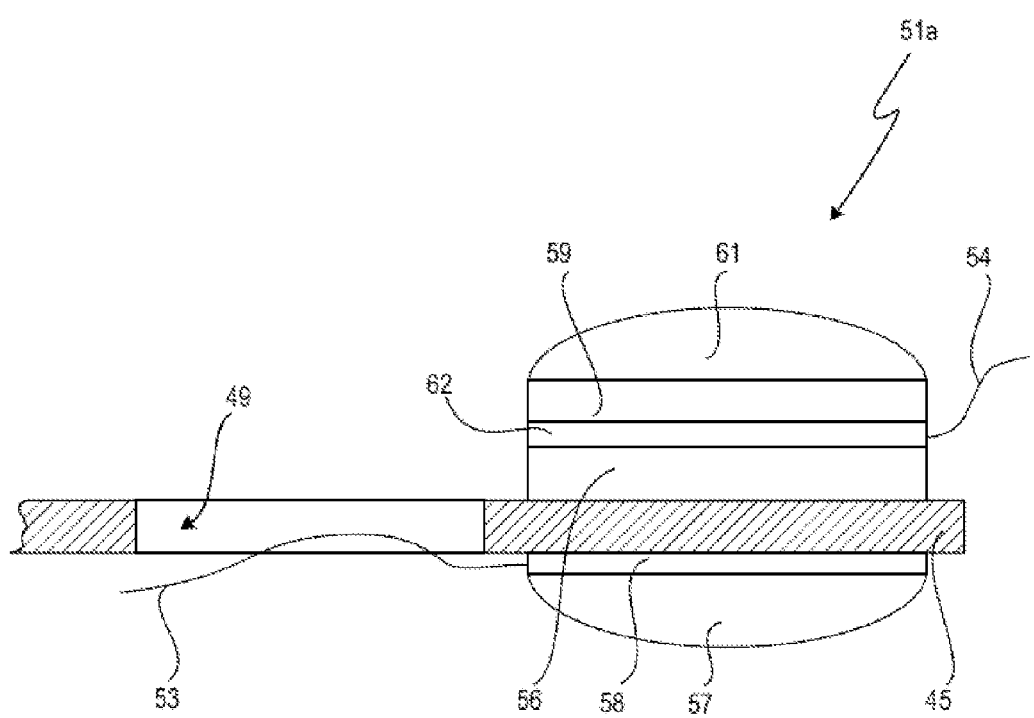
FIG. 6 shows a section through one of the snap fasteners with connection cable and stimulation electrode.

FIG. 6 shows a schematic section through the facemask 45 in the region of the eye hole 49, wherein the snap fastener 51a can be seen in cross section.

The snap fastener 51a comprises a lower part 56, which is attached to the facemask 45 via an attachment part 57. To this end, teeth serve in a fashion known per se, as described in DE 36 11 115 A1, which was mentioned at the outset. A clamping end 58 of the stimulation electrode 53 is arranged and secured between the attachment part 57 and the facemask 45.

The snap fastener 51 furthermore has an upper part 59, which is likewise connected to an attachment part 61. Situated between lower part 56 and upper part 59 there is a connection ear 62 of the connection cable 54 such that when the upper part 59 is clipped onto the lower part 56 the connection cable 54 is fixedly connected to the snap fastener 51a, wherein, at the same time, an electrically conductive connection to the stimulation electrode 53 is ensured.

Since the closed snap fastener 51a is fixedly and immovably secured to the facemask 45, pulling the connection cable 54 does not lead to the stimulation electrode 53 being displaced with respect to the facemask 54.

Furthermore, the facemask 45 is fitted to the head of the patient and secured there in a suitable fashion such that pulling on the connection cable 54 does not lead to the facemask 45 being displaced either with respect to the head of the patient.

As a result of all of this, the stimulation electrode 53, once it has assumed a position, remains therein for the duration of the stimulation such that a reliable and, over time, continuous and unchanging stimulation is ensured.

The stimulation electrode 53 can also be secured above the facemask 45 on the attachment part 57 such that it extends through the eye opening 49 from, as it were, outside of the facemask 45.

FIG. 7 shows another embodiment of the novel device 10", in which the nose part 12, in place of the frames 14 and 15, has eye brackets 71, 72, optionally slightly bent, which extend between the nose bracket 16 and the lateral arms 17 and 18.

In FIG. 7, the same reference signs as in FIGS. 1 and 3 have been used for corresponding features, and so reference is made to the description above in respect of the further details.

In the device 10", the electrode holders 22, 23, 24, 25 are embodied as pins 73, 74, 75, 76, which are made of V2A stainless steel. The pins 73, 74, 75, 76 are attached to the eye brackets 71 and 72 via holders 77, 78, 79, 80 such that they can be adjusted in the longitudinal direction 81 of the pins 73, 74, 75, 76 and can be interchanged if necessary.

In this fashion, the device 10″ is fitted once by a person skilled in the art to the geometry of the patient head such that the stimulation electrodes 26 and 27, running between the pins 73 and 74 or 75 and 76, rest against the eye of the patient as has already been described above.

Since the pins 73, 74, 75, 76 have a rigid design, the stimulation electrodes 26, 27 are placed against the cornea by virtue of the fact that the stimulation electrodes as loops are inserted into the eye-side, inner ends of the pins 73, 74, 75, 76 and are respectively only connected in a mechanically fixed and electrically conductive fashion to the nose-side pin 74 or 75. On the temple-side pin 73 or 76, the stimulation electrode 26 or 27 is routed through an ear 82 to respectively one weight 83 with a sufficient mass to tension the stimulation electrodes 26, 27 such that they are easily tightened and rest against the cornea.

It is easy to exchange the stimulation electrodes 26, 27; they only have to be removed from the ears 82 and detached from the nose-side pins 74, 75.

The nose-side pins 74 and 75 are electrically interconnected via a cable 84, which moreover has a connection to a connection cable 85, the latter being able to be connected to the stimulation instrument 36 via a plug 86. This is how, as it were, the stimulation electrodes 26 and 27 are electrically connected in parallel. The second connection to the stimulation instrument 36 is brought about via a connection cable 87 with plug 88.

This connection cable 87 is secured on the lateral arm 17 via a holder 89 and leads to a counter electrode 91, which is placed against the temple of the patient and hence closes the circuit.

The counter electrode 91 can also be used in conjunction with the facemask 45 from FIG. 5 or a device 10, 10′ from FIGS. 1 and 3, if use is made in those cases either of only one stimulation electrode 26, 27 or of two stimulation electrodes 26, 27 which, like in FIG. 7, are electrically connected in parallel.

Figure 8:
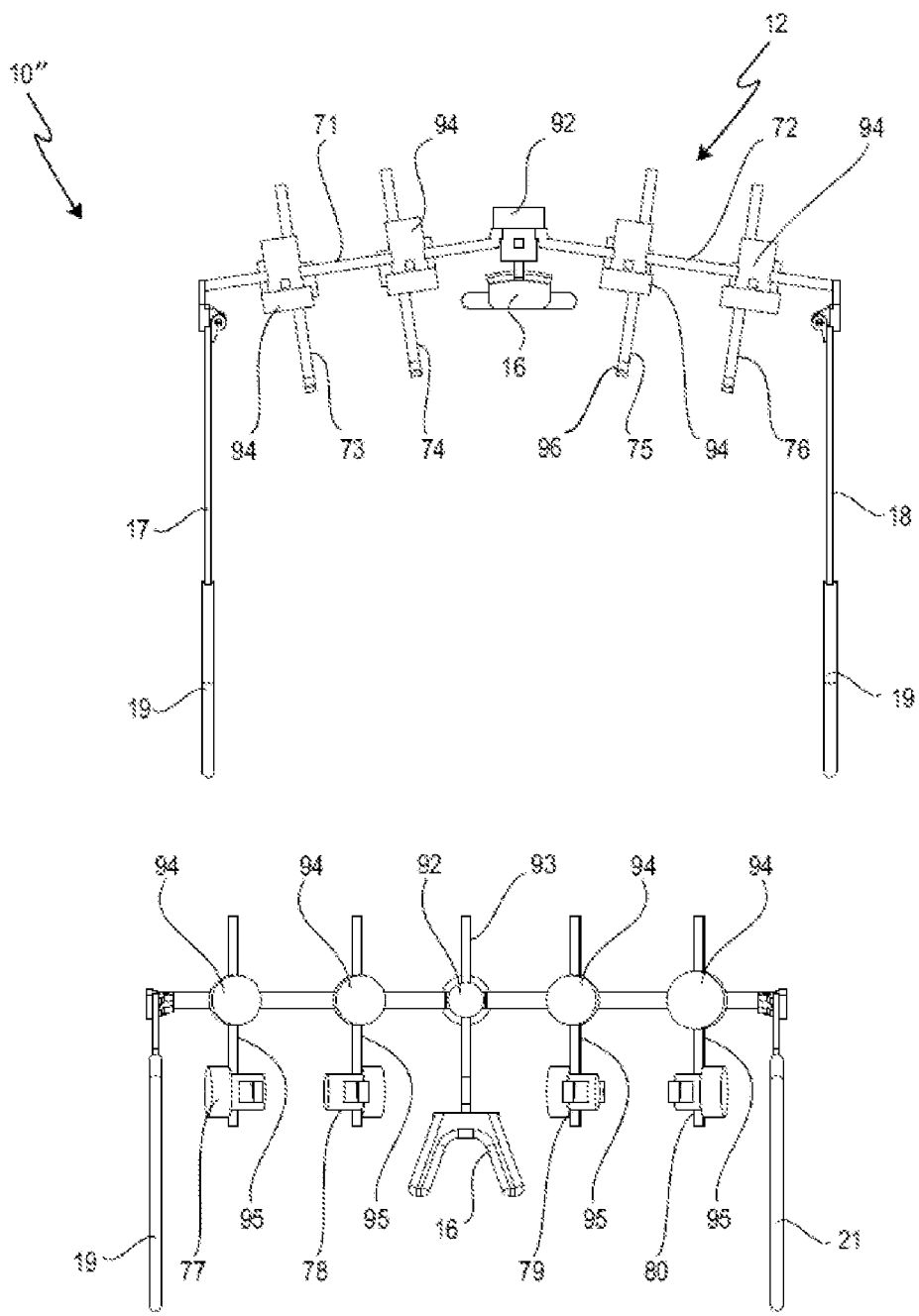
FIG. 8 shows an alternative embodiment of the device from FIG. 7 in a plan view and in a view from the patient.

In FIG. 8, the top shows a plan view and the bottom shows a view from the patient of an alternative embodiment of the device 10″. In this device 10‴, the eye brackets 71, 72 of the nose part 12 have a straight design and are attached on the inside, angled slightly toward the patient at an angle, to a nose holder 92. On the outside, the lateral arms 17, 18, which have already been described, are hinged onto the eye brackets 71, 72.

Attached on the nose holder 92 via a holding pin 93 there is the nose part 16, which can therefore be adjusted with respect to the eye brackets in the longitudinal direction of the holding pin 93 in order to be able to set the level of the nose part 12 with respect to the nose of the patient such that the eye brackets 71, 72 can be aligned in an optimal fashion with respect to his eyes.

Arranged on each eye bracket 71, 72 there respectively are two pin holders 94, which can be displaced along the eye brackets 71, 72 and pivoted about the eye brackets 71, 72. Each pin holder 94 carries a holding pin 95 which is held such that it can be adjusted in the longitudinal direction thereof. The holding pins 95 extend approximately parallel to the holding pin 93.

At their free, lower end, the holding pins 95 respectively carry one of the holders 77, 78, 79, 80, which are known from FIG. 7 and in which respectively one of the V2A pins 73, 74, 75, 76 serving as electrode holder 22, 23, 24, 25 is held in a longitudinally displaceable fashion. At their free end close to the eye, the pins 73, 74, 75, 76 are respectively provided with a receptacle 96, which will still be described in more detail, for the stimulation electrode (not illustrated in FIG. 8).

Eye brackets 71, 72, holding pins 95 and pins 73, 74, 75, 76 run approximately orthogonal to one another, and so the receptacles 96 can be adjusted in all three spatial directions and hence can be fitted without problems to the conditions of the shape of the head, face and eye of the patient. In respect of the usage position of the novel device, eye brackets 71, 72 and pins 73, 74, 75, 76 run approximately horizontally, while the holding pins 93 and 95 run approximately vertically.

Figure 9:
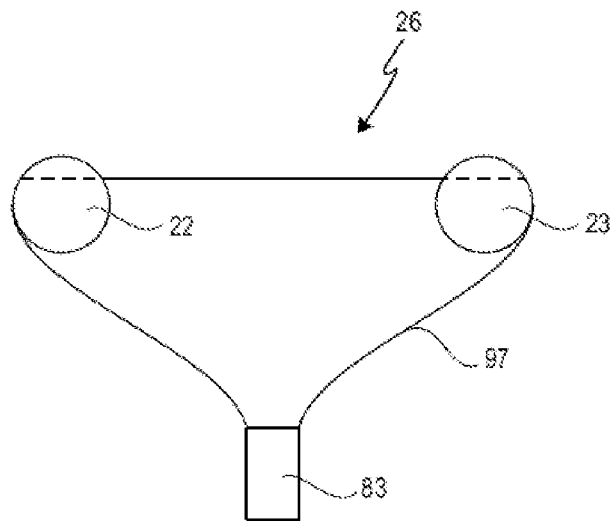
FIG. 9 shows a stimulation electrode loop hooked into two electrode holders and weighed down by a weight.

FIG. 9 shows a stimulation electrode 26, embodied as a loop 97, as can be used in the devices 10, 10″ and 10‴ from FIGS. 1, 3, 7 and 8. This loop 97 is hooked into two electrode holders 22, 23 and tensioned by a weight 83, hanging below and between the electrode holders 22, 23 in the usage position, connected to both ends of the loop 97.

Both the helical springs or elastic pins as per FIGS. 1 to 4 and the rigid pins 73, 74, 75, 76 as per FIG. 7 or 8 can be used as electrode holders 22, 23. These electrode holders 22, 23 have the aforementioned receptacle 34 or 96 at their free end 98 close to the eye, which receptacle in this case has an upwardly open groove 99, in which the loop 97 comes to rest.

Figure 10:
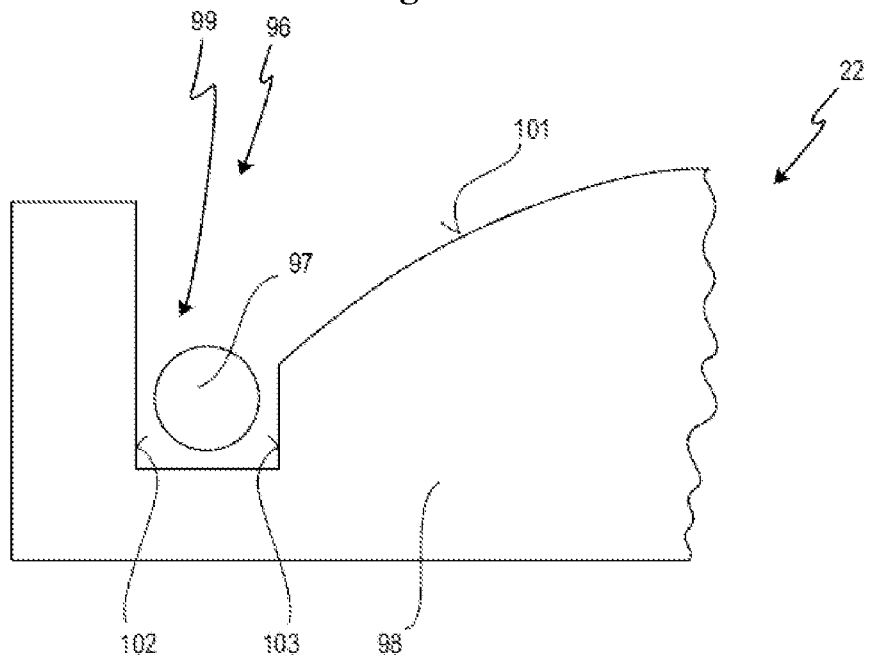
FIG. 10 shows a schematic lateral view of an inner free end of an electrode holder with a receptacle for a stimulation electrode.

In order also to make it possible or easier for patients who are very visually impaired or almost blind to hook in the loop 97, an area 101 running obliquely toward the groove 99 is formed on the electrode holder 22, as shown in FIG. 10 in a greatly magnified illustration which is not true to scale. A loop 87 placed onto the electrode holder 22 therefore automatically slides into the groove 99, where it is held on the side by two perpendicular side walls 102, 103 such that it cannot come free from the groove 99 when the device 10, 10′, 10‴ is put on, even when the stimulation electrode rests against the cornea and, in the process, is tightened by the weight 83.

So that the loop 97 can be electrically contacted, at least one of the electrode holders 22, 23 is manufactured from an electrically well conducting material, wherein the contact resistance to the loop is kept low by virtue of the fact that the loop 97 is pulled into the groove 99 by the weight 83.

The relevant electrode holder 22, 23 is then, as already described above, connected to a cable which serves for the connection to a stimulation instrument 36, as was already described in more detail above.

Therefore, what is claimed is:

1. A device for electrostimulation of the cornea of an eye, comprising a spectacles-like supporting frame which comprises a nose part and an arrangement for holding the supporting frame on the head of the patient, the arrangement being connected to the nose part, at least one interchangeable, wire-shaped stimulation electrode being arranged on the nose part, at least two electrode holders being provided on the nose part, said stimulation electrode extending between said electrode holders and resting on said cornea when said device is positioned on the head of the patient, wherein each of said two electrode holders comprises an elastically resilient, elongate body.

2. The device of claim 1, wherein the stimulation electrode is manufactured from a metallically coated polymer thread.

3. The device of claim 1, wherein the stimulation electrode is connected to at least one of the electrode holders in an electrically conductive fashion.

4. The device of claim 1, wherein, at its free end, each electrode holder is provided with a receptacle for the stimulation electrode.

5. The device of claim 4, wherein the receptacle comprises a groove.

6. The device of claim 5, wherein the at least one stimulation electrode is embodied as a loop, which is connected to a weight and hooked into said grooves of said two electrode holders.

7. The device of claim 1, wherein a cable is connected to at least one of the electrode holders.

8. The device of claim 7, wherein the cable is embodied as connection cable for the direct connection to a stimulation instrument.

9. The device of claim 7, wherein the cable is connected to a connection tab arranged on the device.

10. The device of claim 1, wherein the at least one stimulation electrode is fixedly connected to one of the two electrode holders and is arranged within an ear provided at the other of the two electrode holders, said at least one stimulation electrode subjected to tension by a weight.

11. The device of claim 1, wherein the nose part comprises a nose bracket and at least one frame, on which the two electrode holders are arranged in adjustable fashion.

12. The device of claim 1, wherein the arrangement for holding the supporting frame comprises two lateral arms attached to the nose part.

13. The device of claim 1, wherein a counter electrode is provided for the at least one stimulation electrode.

14. The device of claim 1, wherein two stimulation electrodes are provided and electrically connected in parallel.

15. A device for electrostimulation of the cornea of an eye, comprising a spectacles-like supporting frame which comprises a nose part and an arrangement for holding the supporting frame on the head of the patient, the arrangement being connected to the nose part, at least one interchangeable, wire-shaped stimulation electrode being arranged on the nose part, at least two electrode holders being provided on the nose part, said stimulation electrode extending between said electrode holders and resting on said cornea when said device is positioned on the head of the patient, wherein each of said two electrode holders comprises an elastically resilient, elongate body which, at its one end, comprises a mount for assembling the electrode holder on a frame of the device and, at its other end, comprises a receptacle for a wire-shaped stimulation electrode.

16. The device of claim 15, wherein each electrode holder comprises a mount, by means of which it is arranged on the nose part in an adjustable and interchangeable fashion.

17. The device of claim 16, wherein the mount is arranged in adjustable fashion on the nose part by means of a holding pin.

18. The electrode holder of claim 15, wherein the body is embodied as a helical spring.

19. The device of claim 15, wherein the stimulation electrode comprises a loop made of a metallically coated polymer thread and a weight connected to said loop.

20. A device for electrostimulation of the cornea of an eye, comprising a spectacles-like supporting frame which comprises a nose part and an arrangement for holding the supporting frame on the head of the patient, the arrangement being connected to the nose part, at least one interchangeable, wire-shaped stimulation electrode being arranged on the nose part, at least two electrode holders being provided on the nose part, said stimulation electrode extending between said electrode holders and resting on said cornea when said device is positioned on the head of the patient, wherein the supporting frame is embodied as a facemask, which has an integral design with the nose part, and wherein at least one electrode holder is embodied as a snap fastener with upper part and lower part, wherein the lower part is secured on the facemask.

21. The device of claim 20, wherein the arrangement for holding the supporting frame comprises at least one elastic band.

22. The device of claim 20, wherein the arrangement for holding the supporting frame comprises at least a Velcro™ fastening.

23. The device of claim 20, wherein one of the upper and lower part is connected to a connection cable, which serves for the direct connection to a stimulation instrument.

24. The device of claim 20, wherein the facemask comprises at least one eye opening for an eye of a patient, wherein respectively one snap fastener is arranged on both sides next to the eye opening and the stimulation electrode runs through the eye opening between the two snap fasteners and is held by the snap fasteners.

25. The device of claim 20, wherein a counter electrode is provided for the at least one stimulation electrode.

26. A device for electrostimulation of the cornea of an eye, comprising a spectacles-like supporting frame which comprises a nose part and an arrangement for holding the supporting frame on the head of the patient, the arrangement being connected to the nose part, at least one interchangeable, wire-shaped stimulation electrode being arranged on the nose part, at least two electrode holders being provided on the nose part, said stimulation electrode extending between said electrode holders and resting on said cornea when said device is positioned on the head of the patient, wherein the nose part comprises a nose bracket and at least one eye bracket, on which the two electrode holders are arranged in adjustable fashion, and wherein the nose bracket is arranged in adjustable fashion on a nose holder via a holding pin, on which nose holder two eye brackets are secured, at least one of said eye brackets being provided with two pin holders which sit in displaceable fashion on the eye bracket, each pin holder carrying a height-adjustable holding pin provided each with an electrode pin, which electrode pin is arranged so as to be adjustable in its longitudinal direction and is configured as one of said two electrode holders.

27. A device for electrostimulation of the cornea of an eye, comprising a spectacles-like supporting frame which comprises a nose part and an arrangement for holding the supporting frame on the head of the patient, the arrangement being connected to the nose part, at least one interchangeable, wire-shaped stimulation electrode being arranged on the nose part, at least two electrode holders being provided on the nose part, said stimulation electrode extending between said electrode holders and resting on said cornea when said device is positioned on the head of the patient, wherein each of said two electrode holders comprises an electrically conductive pin, and wherein the at least one stimulation electrode is fixedly connected to one of said two pins, the other of said two pin comprising an ear, the at least one stimulation electrode being guided through said ear and subjected to tension by a weight.

28. The device of claim 27, wherein said electrically conductive pin is made of stainless steel.

* * * * *